United States Patent
Saetveit et al.

(10) Patent No.: US 9,752,691 B1
(45) Date of Patent: Sep. 5, 2017

(54) VALVE FOR CONTROLLED SHUTTLE OF LIQUID INTO MICROTITER PLATES AND MIXING

(71) Applicant: Elemental Scientific, Inc., Omaha, NE (US)

(72) Inventors: Nathan Saetveit, Omaha, NE (US); Daniel R. Wiederin, Omaha, NE (US)

(73) Assignee: Elemental Scientific, Inc., Omaha, NE (US)

(*) Notice: Subject to any disclaimer, the term of this patent is extended or adjusted under 35 U.S.C. 154(b) by 104 days.

(21) Appl. No.: 14/791,336

(22) Filed: Jul. 3, 2015

Related U.S. Application Data

(60) Provisional application No. 62/020,826, filed on Jul. 3, 2014.

(51) Int. Cl.
  *F16K 11/074* (2006.01)
  *H01J 49/04* (2006.01)
  *G01N 35/10* (2006.01)

(52) U.S. Cl.
  CPC ...... *F16K 11/0743* (2013.01); *H01J 49/0495* (2013.01); *G01N 35/1097* (2013.01)

(58) Field of Classification Search
  CPC .................. F16K 11/074; G01N 30/20; G01N 2030/201; G01N 2030/202; G01N 35/1097
  USPC .................................... 137/625.46
  See application file for complete search history.

(56) References Cited

U.S. PATENT DOCUMENTS

| | | | | |
|---|---|---|---|---|
| 4,444,066 A | * | 4/1984 | Ogle | G01N 30/20 73/61.56 |
| 4,625,569 A | * | 12/1986 | Toei | G01N 30/20 73/863.72 |
| 6,012,487 A | * | 1/2000 | Hauck | F16K 11/0743 137/625.11 |
| 6,012,488 A | * | 1/2000 | Nichols | F16K 11/0743 137/625.11 |
| 6,662,826 B1 | * | 12/2003 | Kokawa | F16K 11/074 137/597 |
| 6,958,119 B2 | * | 10/2005 | Yin | G01N 30/34 210/101 |
| 8,322,197 B2 | * | 12/2012 | Koster | G01N 30/20 73/61.55 |
| 8,944,102 B1 | * | 2/2015 | Wiederin | F16K 11/0743 137/625.46 |
| 9,146,182 B1 | * | 9/2015 | Wiederin | G01N 30/20 |
| 9,541,207 B1 | * | 1/2017 | Saetveit | F16K 11/0743 |
| 2010/0058841 A1 | * | 3/2010 | Wilen | F16K 11/0743 73/61.56 |

* cited by examiner

*Primary Examiner* — John Fox
(74) *Attorney, Agent, or Firm* — Advent, LLP

(57) ABSTRACT

Valve assemblies are described that provide segmented shuttle of liquid into sample vessels and automatic mixing via bubbles in the segmented liquid. A valve assembly includes a first valve member having ports configured to receive a pressurized gas, a first fluid, and a second fluid. The valve assembly also includes a second valve member coupled adjacent to the first valve member. The second valve member comprises a plurality of channels configured to interface with the first valve member. In a first configuration, the first fluid is loaded into an external loop. In the second configuration, the second fluid is eluted from the column into a vial in a segmented stream via bubbles of pressurized gas. Bubbles of gas automatically mix the eluted sample fluid.

14 Claims, 8 Drawing Sheets

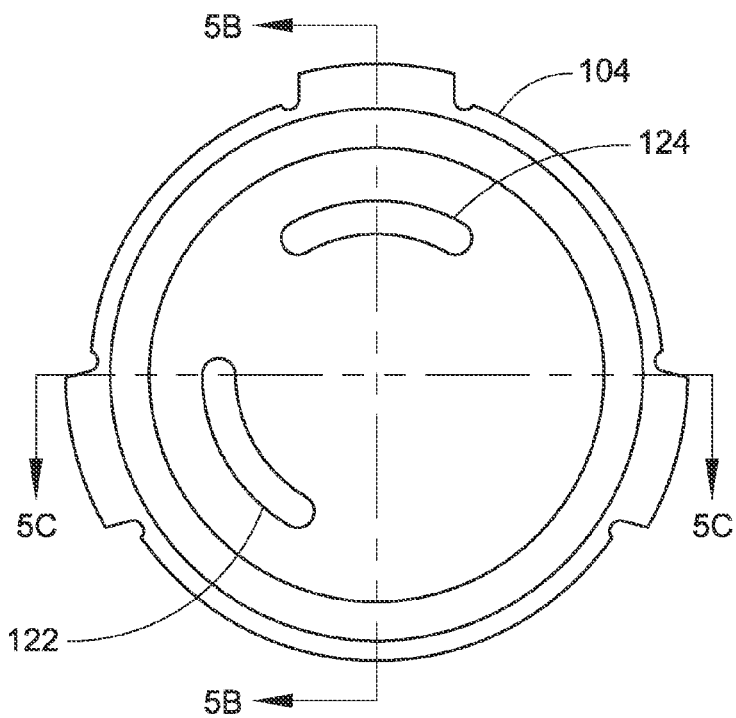
FIG. 5A
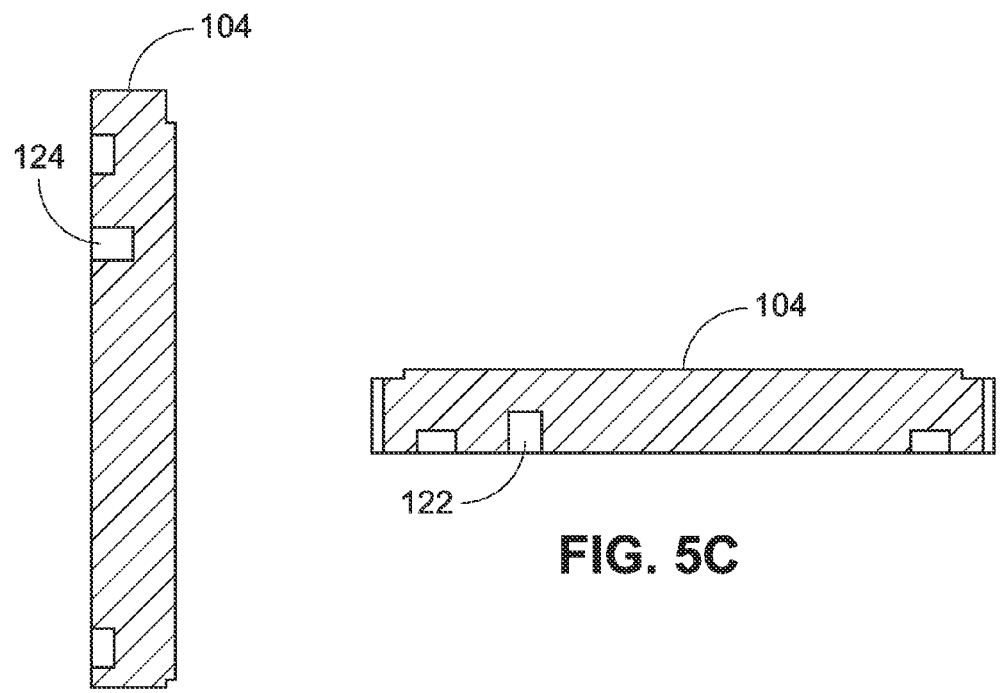
FIG. 5B
FIG. 5C

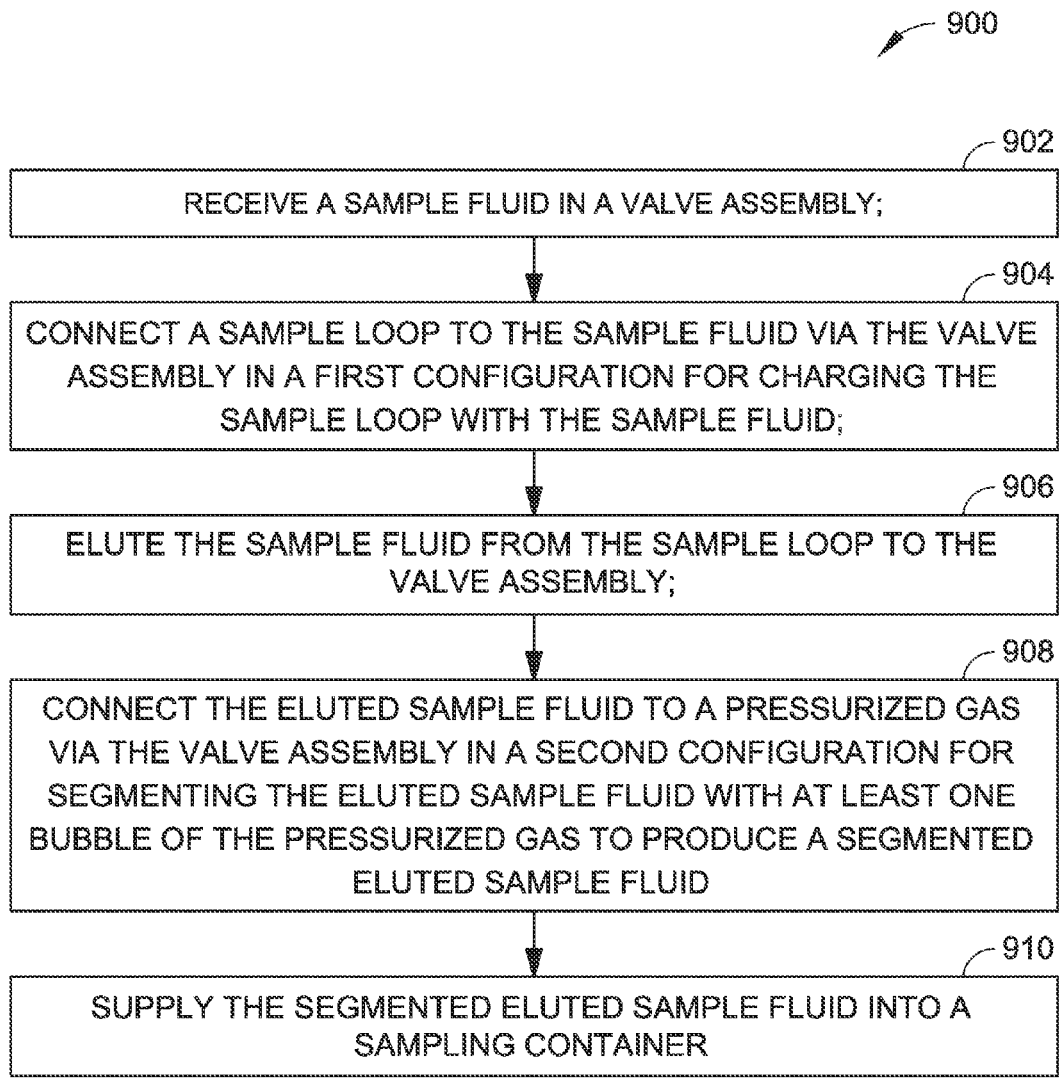

US 9,752,691 B1

VALVE FOR CONTROLLED SHUTTLE OF LIQUID INTO MICROTITER PLATES AND MIXING

CROSS-REFERENCE TO RELATED APPLICATIONS

The present application claims the benefit under 35 U.S.C. §119(e) of U.S. Provisional Application Ser. No. 62/020,826, filed Jul. 3, 2014, and titled "VALVE FOR CONTROLLED SHUTTLE OF LIQUID INTO MICROTITER PLATES AND MIXING," which is herein incorporated by reference in its entirety.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Valve assemblies are described that provide segmented shuttle of liquid into microtiter plates, and mixing of the liquid. A valve assembly includes a first valve member having ports configured to receive a pressurized gas, a first fluid, and a second fluid. The valve assembly also includes a second valve member coupled adjacent to the first valve member. The second valve member comprises a plurality of channels configured to interface with the first valve member. In a first configuration, the first fluid is loaded into an external loop. In the second configuration, the second fluid is eluted from the column into a vial in a segmented stream via bubbles of pressurized gas. Bubbles of gas automatically mix the eluted sample fluid.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 5A is a top plan view of a rotor for a multiport flow valve assembly in accordance with an example embodiment of this disclosure.

FIG. 5B is a partial cross-sectional side elevation view of the rotor illustrated in 5A.

FIG. 5C is another partial cross-sectional side elevation view of the rotor illustrated in 5A.

FIG. 9 is a flow diagram of a method for producing a segmented fluid stream, such as to provide mixing of the segmented fluid stream in a sampling container, in accordance with an example embodiment of the present disclosure.

DETAILED DESCRIPTION

Overview

Figure 1:
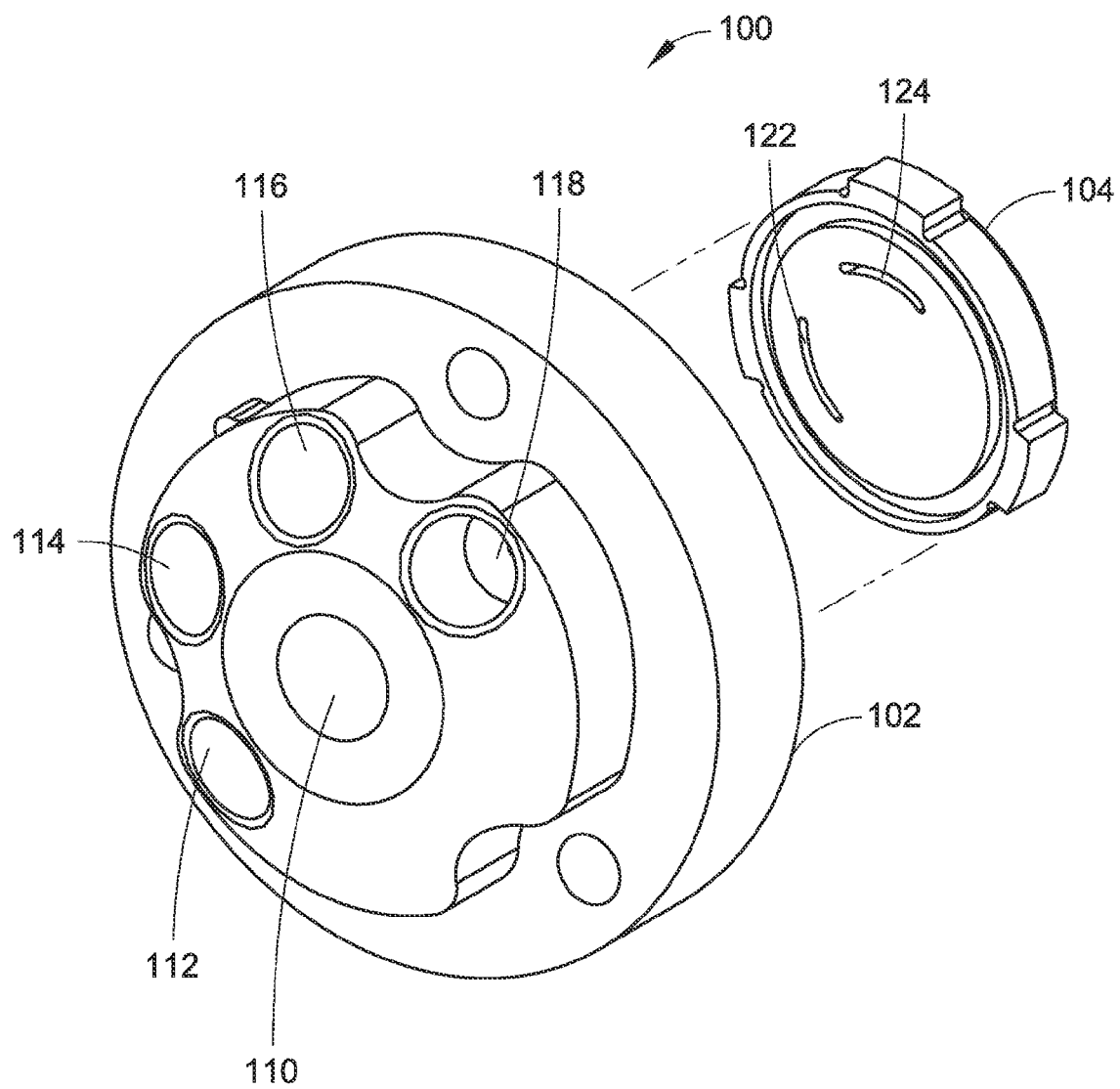
FIG. 1 is an exploded isometric view illustrating a multiport flow valve assembly including a rotor, and a stator, in accordance with an example embodiment of the present disclosure.
Figure 2:
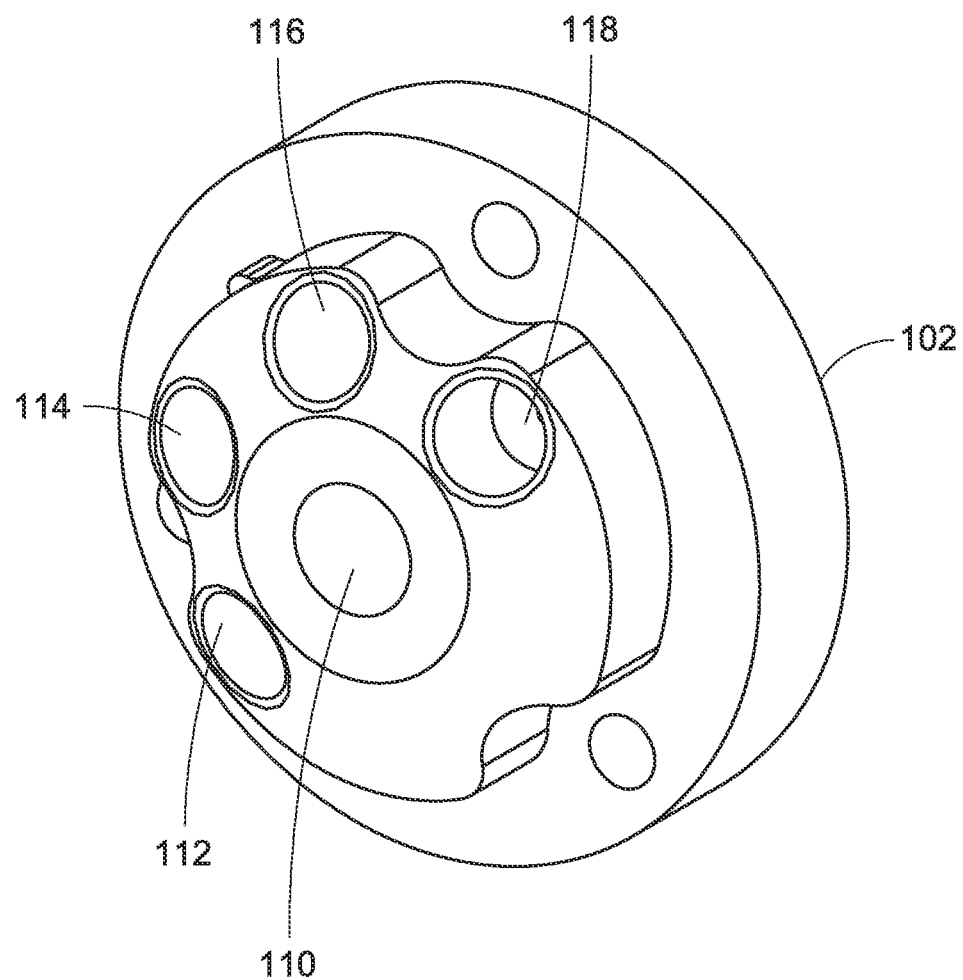
FIG. 2 is an isometric view illustrating a stator for a multiport flow valve assembly in accordance with an example embodiment of the present disclosure.
Figure 3:
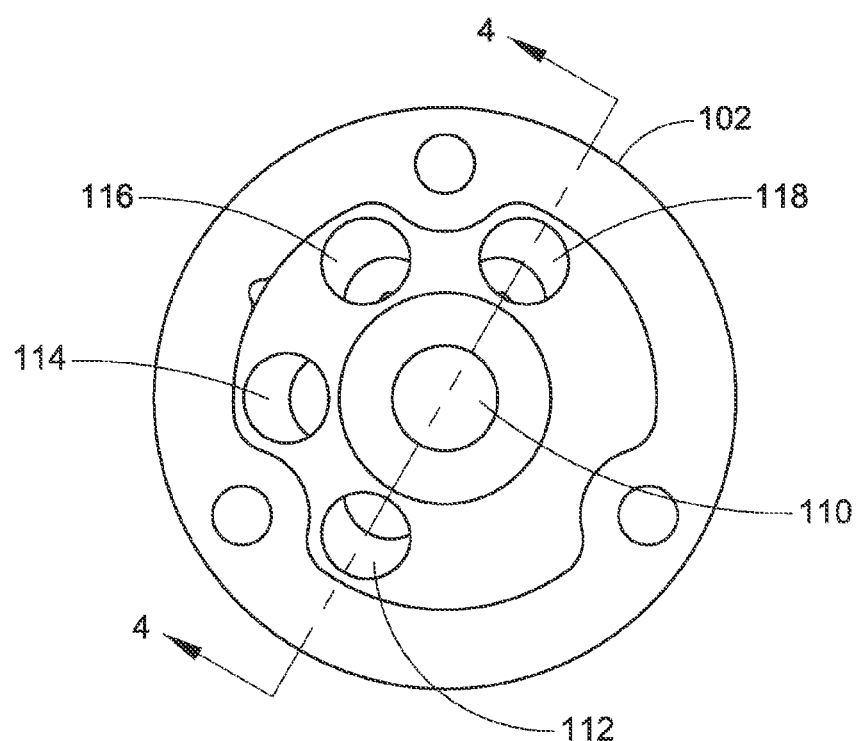
FIG. 3 is a front view of the stator illustrated in FIG. 2.
Figure 4:
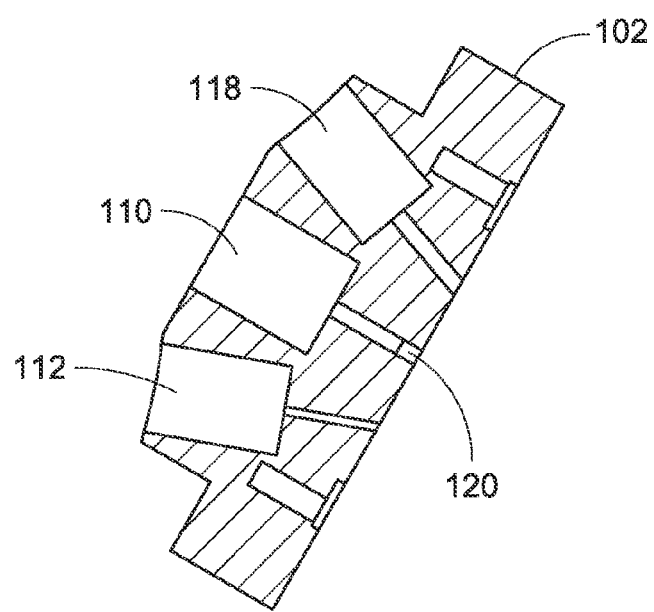
FIG. 4 is a cross-sectional side view of the stator illustrated in FIG. 2.
Figure 6:
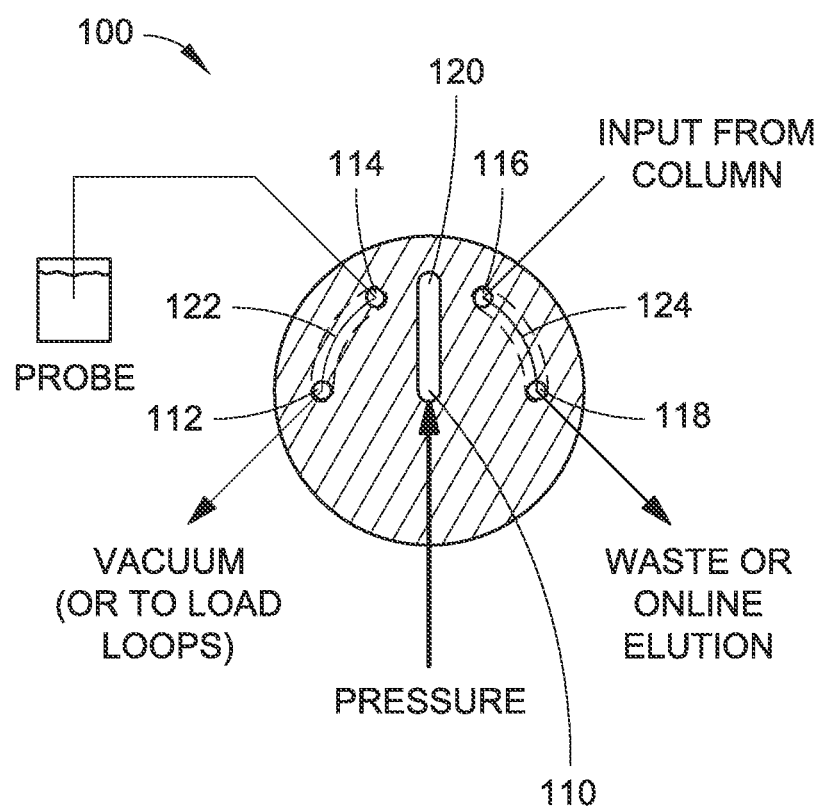
FIG. 6 is a diagrammatic illustration of a system including a multiport flow valve assembly, such as the multiport flow valve assembly illustrated in FIG. 1, where the multiport flow valve assembly is arranged in a load configuration in accordance with an example embodiment of the present disclosure.
Figure 7:
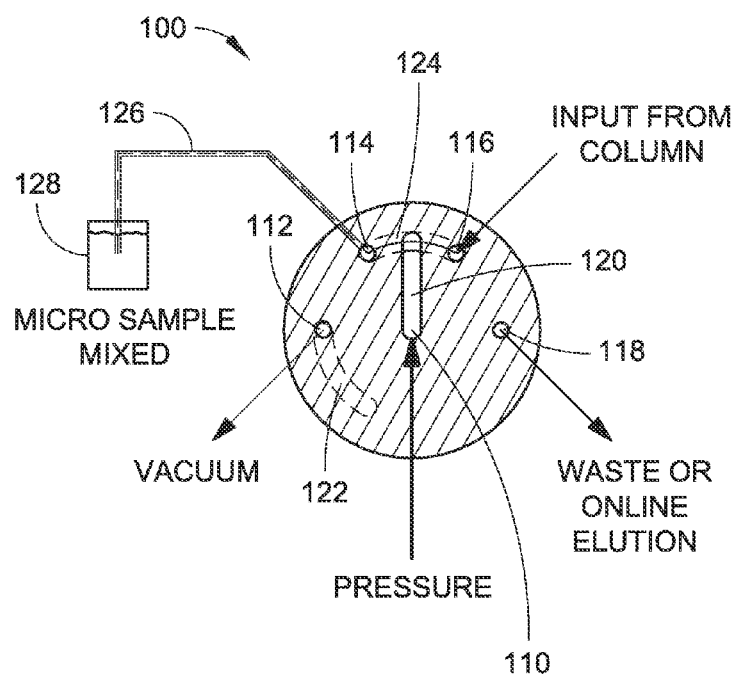
FIG. 7 is a diagrammatic illustration of a system including a multiport flow vale assembly, such as the multiport flow valve assembly illustrated in FIG. 1, where the multiport flow valve assembly is arranged in an inject configuration in accordance with an example embodiment of the present disclosure.

Multiport valves are typically used to transport sample materials to laboratory equipment for analysis. For example, multiport valves can be used to introduce liquid samples into ICP spectrometry instrumentation for analysis. Multiport valves can also be used to load samples on columns for liquid and/or gas chromatography. Typical valves used in these applications include six-port (6-port), two-position (2-position) rotary valves. Generally, two ports of a rotary valve are connected to an external (e.g., sample) loop, where one port is connected to a sample source, and another port is connected to a carrier source. A further port can be connected to a vent (e.g., waste), with another port connected to a nebulizer/column. When the valve is in a first configuration, sample from the sample source flows through the sample loop, while carrier from the carrier source flows directly to a nebulizer/column. When the valve is rotated to a second configuration, the carrier source is connected to the sample loop for injecting the sample contained in the sample loop into the nebulizer or onto the column. In some multiport valve configurations, one fluid is mixed with another fluid by injecting the two fluids into separate ports of a multiport valve.

Valve assemblies are described that provide segmented shuttling of liquid into microtiter plates and automatic mixing of the liquid. In embodiments, a valve assembly includes a first valve member (e.g., a stator) having a first port configured to receive a pressurized gas (e.g. argon, nitrogen, or other inert gas or mixture of gases), a second port configured to connect to a vacuum or external loop (e.g., a sample loop), a third port configured to receive a first fluid (e.g., a sample fluid), a fourth port configured to receive a second fluid (e.g., an eluted sample fluid) received from an input (e.g., a column), and a fifth port configured to connect to a vent (e.g., waste). In embodiments, the first port is connected to a channel. The valve assembly also includes a second valve member (e.g., a rotor) coupled adjacent to the first valve member. The second valve member comprises a plurality of channels configured to interface with the first valve member so that the second port is connected to the third port and the fourth port is connected to the fifth port in a first configuration (e.g., a load configuration), and the third port is connected to the fourth port and the channel of the first port is connected to the channel of the second valve member that connects the third and fourth ports in a second configuration (e.g., an inject configuration). In the first (load) configuration, the first fluid is loaded into the external loop. In the second (inject) configuration, the second fluid is eluted from the column into a sampling container sampling container (e.g., microtiter plate, sample cup, vial) in a segmented stream via pressurized gas. Segmenting the stream of eluted sample allows for controlled delivery to sampling containers. Gas bubbles used to segment the stream also provide automatic mixing of the eluted sample fluid in the sampling containers.

Example Implementations

Referring generally to FIGS. 1 through 7, a valve assembly 100 is described. The valve assembly 100 includes a first valve member and a second valve member coupled adjacent to the first valve member. As shown, the valve assembly 100 can be configured as a rotary valve assembly having a first valve member comprising a stator 102 and a second valve member comprising a rotor 104 coupled adjacent to the stator 102 so that it can rotate with respect to the stator 102. It should be noted that while the accompanying figures show the stator 102 and the rotor 104 of the valve assembly 100, the valve assembly 100 may also include additional components, such as components for holding the rotor 104 adjacent to the stator 102, and so forth. For example, the valve assembly 100 may further include a drive configured to rotate the rotor 104 and/or the stator 102, and a housing configured to support the stator 102 and/or the rotor 104 adjacent to the stator 102.

The stator 102 includes ports configured to connect to an external loop (e.g., a sample loop) and a vent (e.g., waste). The stator 102 is configured to receive a pressurized gas (e.g. argon, nitrogen, or other inert gas or mixture of gases), a first fluid (e.g., a sample fluid), and a second fluid (e.g., an eluted sample fluid). The stator 102 generally includes a first port 110, a second port 112, a third port 114, a fourth port 116, and a fifth port 118. The first port 110 is configured to receive the pressurized gas, which can facilitate segmenting a fluid via gas bubbles, as described herein. The second port 112 is configured to connect to the external loop (e.g., sample loop). The third port 114 is configured to receive the first fluid (e.g., sample fluid). The fourth port 116 is configured to receive the second fluid (e.g., eluted sample fluid) from an input (e.g., a column, such as a preconcentration column, a cleanup column, or so forth). The fifth port 118 configured to connect to the vent. The stator 102 also includes a channel 120 connected to the first port 110 (e.g., as shown at least in FIGS. 4, 6, and 7). The channel 120 facilitates passage of the pressurized gas received by port 110 to other portions of the valve assembly 100. For example, the channel 120 can introduce the pressurized gas to a fluid flow that is transferred from the fourth port 116 to the third port 114 via another channel, described further herein. In implementations, fluid flow to the ports of the stator 102 can be controlled using an instrument such as a valve controller (not shown).

The rotor 104 includes channels configured to connect the sample loop to the sample fluid in a first configuration (e.g., a load configuration) for charging the sample loop with the sample fluid, and to connect the eluted sample fluid to the pressurized gas via the valve assembly in a second configuration (e.g., an inject configuration) for supplying a segmented stream of the eluted sample fluid into a sampling container (e.g., a microtiter plate, a sample cup, a sample vial, or so forth). In implementations, the pressurized gas received by the first port 110 and transferred by channel 120 introduces one or more bubbles to fluid flow that is transferred from the fourth port 116 to the third port 114 to form a segmented fluid stream, such as a segmented stream of the eluted sample fluid. The rotor 104 includes a first channel 122 and a second channel 124, which are configured for passage of fluids, where the orientation of the rotor 104 with respect to the stator 102 influences the interaction between the first channel 122 and the second channel 124 with respect to the ports (e.g., the first port 110, the second port 112, the third port 114, the fourth port 116, and the fifth port 118). For example, the first channel 122 is configured to connect the second port 112 to the third port 114 in the first configuration (e.g., a load configuration), and the second channel 124 is configured to connect the fourth port 116 to the fifth port 118 in the first configuration. In a second configuration (e.g., an inject configuration), the second channel 124 is configured to connect the third port 114 to the fourth port 116. In the second configuration, the channel 120 connected to the first port 120 is in fluid communication with the second channel 124, where the second channel 124 is positioned to connect the third port 114 and the forth port 116 in the second configuration. For example, at least a portion of the channel 120 interacts with the second channel 124 such that pressurized gas received by the first port 110 can travel through the channel 120 and into the second channel 124 to segment the second fluid (e.g., eluted sample fluid) traveling from the fourth port 116 to the third port 114 via formation of one or more bubbles that separate respective portions of the second fluid for form a segmented fluid stream 126. In implementations, the segmented fluid stream travels from the third port 114 to a sampling container 128 (e.g., a microtiter plate, a sample cup, a sample vial, or so forth), where bubbles present in the segmented fluid stream, such as the bubbles introduced by the pressurized gas via channel 120) can mix the fluid within the sampling container 128. In implementations, the sample loop can be loaded by vacuum, such as via connection of a vacuum to the second port 112. In implementations, the pressurized gas may comprise an inert gas, such as argon, nitrogen, and so forth, or a combination or mixture of gases. In some embodiments, the fifth port 118 can be connected to a laboratory analysis device, such as an ICPMS or so forth. In these embodiments, the fourth port 116 can be connected to the fifth port 118 via the second channel 124 to furnish online elution of the sample fluid.

Figure 8:
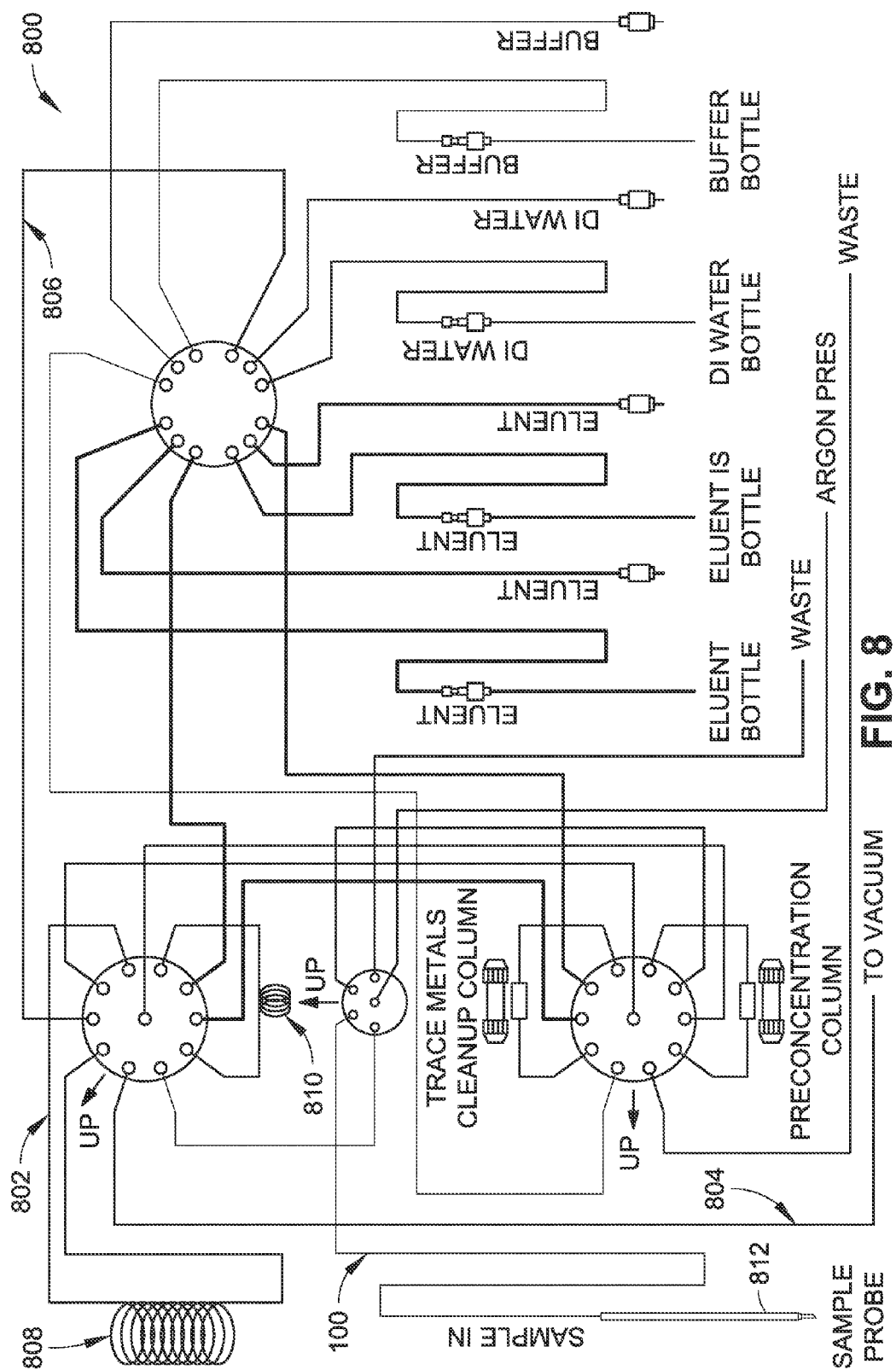
FIG. 8 is a diagrammatic illustration of a system including a multiport flow valve assembly, such as the multiport flow valve assembly illustrated in FIG. 1, in accordance with an example embodiment of the present disclosure.

FIG. 8 illustrates that in some implementations, the valve assembly 100 may be incorporated into a system in which at least one additional multiport flow valve is connected. For example, system 800 includes the valve assembly 100 in fluid communication with a first multiport flow valve 802 and a second multiport flow valve 804. The first multiport flow valve 802 and the second multiport flow valve 804 are in fluid communication with each other via a third multiport flow valve 806, which in turn can provide access to eluent fluid, internal standards, rinse agents, buffers, and so forth.

It should be noted that while the terms "stator" and "rotor" are used herein to describe the first and second valve members, these terms are provided by way of example only (e.g., to illustrate how these components interface (e.g., rotate) with respect to one another), and are not meant to limit how the valve members can be actuated with respect to an external reference (e.g., valve mounting hardware, or the like). Thus, in one particular example, a component described as a "stator" may remain substantially stationary (e.g., with respect to an external reference, such as valve mounting hardware), and a component described as a "rotor" may rotate with respect to the stator. However, in another particular example, a component described as a "stator" may rotate with respect to a rotor, and a component described as a "rotor" may remain substantially stationary (e.g., with respect to valve mounting hardware). Further, in some implementations, both a component described as a "stator" and a component described as a "rotor" may rotate with respect to an external reference.

Example Procedures

Referring now to FIG. 9, example techniques for producing a segmented fluid stream, such as to provide mixing of the segmented fluid stream in a sampling container, are described.

FIG. 9 depicts a process 900, in an example implementation, for producing a segmented fluid stream using, for example, the valve assembly 100 illustrated in FIGS. 1-7 and described above. In the process 900 illustrated, a sample fluid is received in a valve assembly (Block 902). For example, the third port 114 of the stator 102 can receive the sample fluid. Process 900 also includes connecting a sample loop to the sample fluid via the valve assembly in a first configuration for charging the sample loop with the sample fluid (Block 904). For example, the first channel 122 can connect the third port 114 with the second port 112 to charge a sample loop with the sample fluid. FIG. 8 depicts system 800 having a first sample loop 808 and a second sample loop 810, either or both of which can be charged with a sample, such as a sample obtained via sample probe 812. Process 900 further includes eluting the sample fluid from the sample loop to the valve assembly (Block 906). For example, the sample can be eluted from the sample loop to the fourth port 116 of the valve assembly 100. Process 900 further includes connecting the eluted sample fluid to a pressurized gas via the valve assembly in a second configuration for segmenting the eluted sample fluid with at least one bubble of the pressurized gas to produce a segmented eluted sample fluid (Block 908). For example, when the valve assembly 100 is the in second configuration, the second channel 124 connects the fourth port 116 with the third port 114, and the channel 120 of the stator 102 is in fluid communication with each of the pressurized gas (via the first port 102) and the second channel 124 to segment the eluted fluid traveling from the fourth port 116 to the third port 114 with bubbles of the pressurized gas. Process 900 further includes supplying the segmented eluted sample fluid into a sampling container (Block 910). For example, the segmented eluted sample can leave the valve assembly 100 via the third port 114 to be deposited in the sampling container 128, whereby the bubbles used to segment the eluted sample automatically mix the eluted sample within the sampling container 128.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A valve assembly comprising:
   a first valve member having a first port configured to connect to a pressurized gas, a channel connected to the first port, a second port configured to connect to at least one of an external loop or vacuum, a third port configured to connect to a sample fluid, a fourth port configured to connect to an eluted sample fluid, and a fifth port configured to connect to at least one of waste or an online elution; and
   a second valve member coupled adjacent the first valve member and having at least a first channel and a second channel configured to interface with the first valve member so that the second port is connected to the third port via the first channel in a first configuration and the fourth port is connected to the fifth port via the second channel in the first configuration, the third port is connected to the fourth port via the second channel in a second configuration, and the channel connected to the first port is in fluid communication with the second channel connecting the third port and the fourth port in the second configuration for supplying the pressurized gas to the eluted sample fluid to provide a segmented fluid.

2. The valve assembly as recited in claim 1, wherein the first configuration comprises a load configuration and the second configuration comprises an inject configuration.

3. The valve assembly as recited in claim 1, wherein the first valve member comprises a stator and the second valve member comprises a rotor coupled adjacent to the stator.

4. The valve assembly as recited in claim 1, wherein the external loop comprises a sample loop.

5. The valve assembly as recited in claim 1, wherein the pressurized gas is at least one of argon gas or nitrogen gas.

6. The valve assembly as recited in claim 1, wherein the fifth port is connected to an inductively coupled plasma mass spectrometer.

7. The valve assembly as recited in claim 1, wherein the third port is connected to a sampling container when in the second configuration.

8. A valve assembly comprising:
   a first valve member having a first port configured to connect to a pressurized gas, a channel connected to the first port, a second port configured to connect to at least one of an external loop or vacuum, a third port configured to connect to a sample fluid, a fourth port configured to connect to an eluted sample fluid, and a fifth port configured to connect to at least one of waste or an online elution; and a second valve member rotatably coupled respective to the first valve member and configured to transition between at least a first configuration and a second configuration, the second valve member having at least a first channel and a second channel configured to interface with the first valve member so that the second port is connected to the third port via the first channel in the first configuration and the fourth port is connected to the fifth port via the second channel in the first configuration, the third port is connected to the fourth port via the second channel in the second configuration, and at least a portion of the channel of the first valve member is connected to the second channel connecting the third port and the fourth port in the second configuration for supplying the pressurized gas to the eluted sample fluid to provide a segmented fluid.

9. The valve assembly as recited in claim 8, wherein the first configuration comprises a load configuration and the second configuration comprises an inject configuration.

10. The valve assembly as recited in claim 8, wherein the first valve member comprises a stator and the second valve member comprises a rotor coupled adjacent to the stator.

11. The valve assembly as recited in claim 8, wherein the external loop comprises a sample loop.

12. The valve assembly as recited in claim 8, wherein the pressurized gas is at least one of argon gas or nitrogen gas.

13. The valve assembly as recited in claim 8, wherein the fifth port is connected to an inductively coupled plasma mass spectrometer.

14. The valve assembly as recited in claim 8, wherein the third port is connected to a sampling container when in the second configuration.

* * * * *